(12) United States Patent
Piccionelli et al.

(10) Patent No.: US 8,840,401 B2
(45) Date of Patent: Sep. 23, 2014

(54) NETWORK COACHING METHOD

(75) Inventors: Gregory A. Piccionelli, Westlake Village, CA (US); Michael M. Gerardi, Menifee, CA (US)

(73) Assignee: Koletry Processing L.L.C., Dover, DE (US)

( * ) Notice: Subject to any disclaimer, the term of this patent is extended or adjusted under 35 U.S.C. 154(b) by 0 days.

(21) Appl. No.: 12/156,573

(22) Filed: Jun. 2, 2008

(65) Prior Publication Data
US 2008/0242514 A1    Oct. 2, 2008

Related U.S. Application Data

(63) Continuation of application No. 10/822,151, filed on Apr. 9, 2004, now abandoned.

(60) Provisional application No. 60/462,370, filed on Apr. 11, 2003.

(51) Int. Cl.
*G06Q 10/10* (2012.01)
*G06Q 50/22* (2012.01)

(52) U.S. Cl.
CPC ............................ *G06Q 10/10* (2013.01); *G06Q 50/22* (2013.01)
USPC .......................................................... 434/247

(58) Field of Classification Search
USPC ................... 434/247, 236, 238, 127; 482/9
See application file for complete search history.

(56) References Cited

U.S. PATENT DOCUMENTS

| | | | |
|---|---|---|---|
| 6,513,532 B2 * | 2/2003 | Mault et al. | 600/595 |
| 7,056,265 B1 | 6/2006 | Shea | |
| 2002/0022551 A1 | 2/2002 | Watterson et al. | |
| 2002/0055857 A1 | 5/2002 | Mault | |
| 2002/0091796 A1 * | 7/2002 | Higginson et al. | 709/218 |
| 2005/0233861 A1 * | 10/2005 | Hickman et al. | 482/8 |

OTHER PUBLICATIONS

Super Step Safely. From the Internet. <accessed Jun. 21, 1997> <http://web.archive.org/web/*/http://www.primusweb.com/fitnesspartner/library/activity/superste.htm>.

* cited by examiner

*Primary Examiner* — Robert J Utama

(57) ABSTRACT

A method of obtaining advice pertaining to a fitness-related activity performed by a user is provided. A user accesses a central site via a network, such as the Internet, then visits a physical location associated with a fitness-related activity. Information identifying the location is provided to the central site. The user then receives live advice pertaining to the fitness-related activity from a personal advisor, via the network from the central site. Fitness-related activities for which advice is provided include, for example, use of exercise equipment, consumption of foods or beverages, and engagement in other activities having an impact on a user's physical, mental or spiritual well-being.

36 Claims, 3 Drawing Sheets

NETWORK COACHING METHOD

This application is a continuation of U.S. patent application Ser. No. 10/822,151, filed Apr. 9, 2004 now abandoned, which in turn was based on U.S. Provisional Patent Application Ser. No. 60/462,370, filed Apr. 11, 2003, the entire disclosures of each of which are incorporated herein by reference.

FIELD OF THE INVENTION

The present invention relates to a method of obtaining advice via a network, such as the Internet, pertaining to a fitness-related activity.

BACKGROUND OF THE INVENTION

Modern society is increasingly aware of the benefits of a proper diet and regular exercise. However, although awareness of these benefits has increased, many people find it difficult to maintain a proper diet and/or to exercise regularly and correctly. This can be due to lack of time, lack of knowledge regarding dieting and nutrition, or lack of motivation to persevere in an exercise program.

A need exists for a method of obtaining advice that will facilitate maintenance of a diet or nutrition plan.

A need also exists for a method of obtaining advice pertaining to exercising, more specifically to the proper use of exercise equipment, and for motivating the use of such equipment.

SUMMARY OF THE PREFERRED EMBODIMENTS

In accordance with one aspect of the present invention, there is provided a method of obtaining advice pertaining to a fitness-related activity that includes the steps of accessing a central site via a network; visiting a physical location associated with a fitness-related activity; providing information identifying the location to the central site; and receiving advice via the network from the central site pertaining to the fitness-related activity.

In particular embodiments, the inventive method provides a user with diet or nutritional information, more specifically pertaining to foods or beverages that are to be consumed at a restaurant, bar or other physical location serving such items. Additionally, the inventive method provides the user with motivation to eat and drink those foods and beverages that are part of the user's diet or nutrition plan, and to avoid consumption of foods and beverages outside of the user's plan.

In other particular embodiments, the inventive method provides a user with information pertaining to exercise devices that are located in a health club or other location where exercises are performed. This information can include instructions on proper use of the apparatus, including weights, number of repetitions and the like, as well as motivation to perform exercises using the selected apparatus.

According to another aspect of the present invention, a method of obtaining advice pertaining to an activity includes the steps of: visiting a physical location associated with an activity; accessing a central site via a network; providing information identifying the location to the central site; and receiving advice via the network from the central site pertaining to the activity.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

DETAILED DESCRIPTION OF THE PREFERRED EMBODIMENTS

As used herein, a "fitness-related activity" is an activity that affects the physical condition of the user, and more particularly, an activity selected from eating and exercising.

Figure 1:
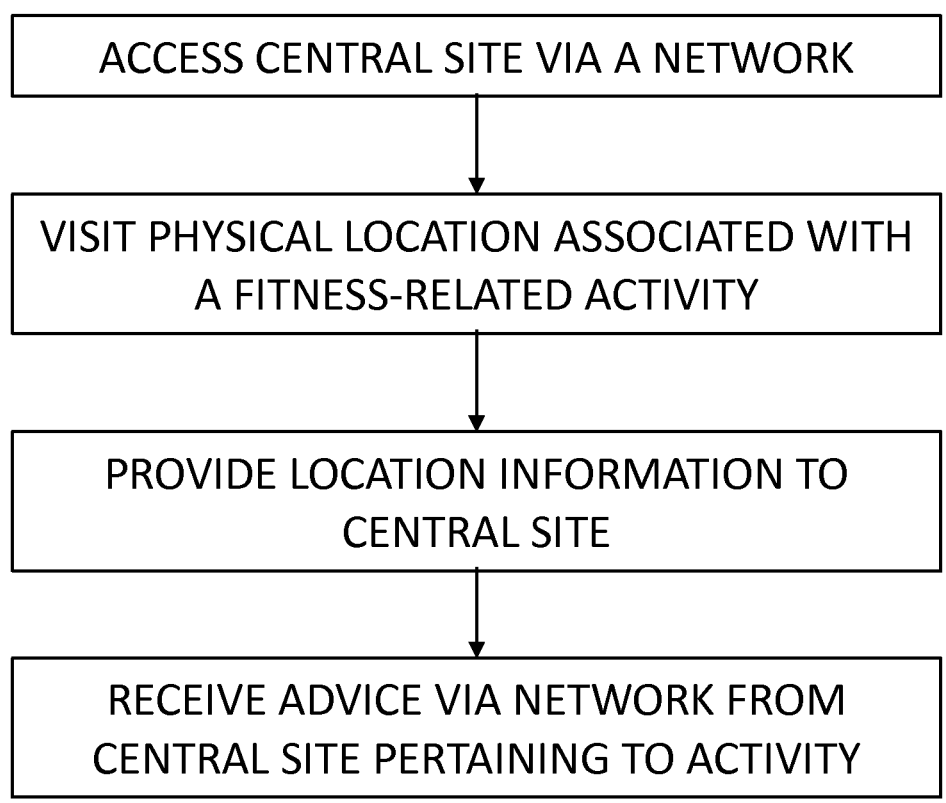
FIG. 1 is a flowchart illustrating a general method according to the invention.

FIG. 1 illustrates a method according to the present invention in its most general aspect. Initially, a user accesses a central site via a network such as the Internet. The central site can be, for example, a site maintained by an organization with which the user has a membership, or a publicly accessible site which can be used without charge or by payment of a fee. In particular embodiments, the user accesses the central site using a PDA, cellular telephone or other portable device that enables Internet access.

After accessing the central site, the user next visits a physical location associated with a fitness-related activity, such as eating, exercising, etc. The user then provides the central site with location information, for example, GPS coordinates, codes, and the like. In particular embodiments, the user also provides the central site with additional information, such as the type of location and the activity in which the user will engage at the location.

Based on the location information which the user has provided, the central site then provides information and/or advice pertaining to the fitness-related activity to the user via the network. The information can be in any form, for example, a computer-generated text or audio message, or a recorded or live message from a personal advisor assigned to the user (an "e-coach"). Alternatively, the central site can arrange for one or more e-coaches to directly contact the user.

Figure 2:
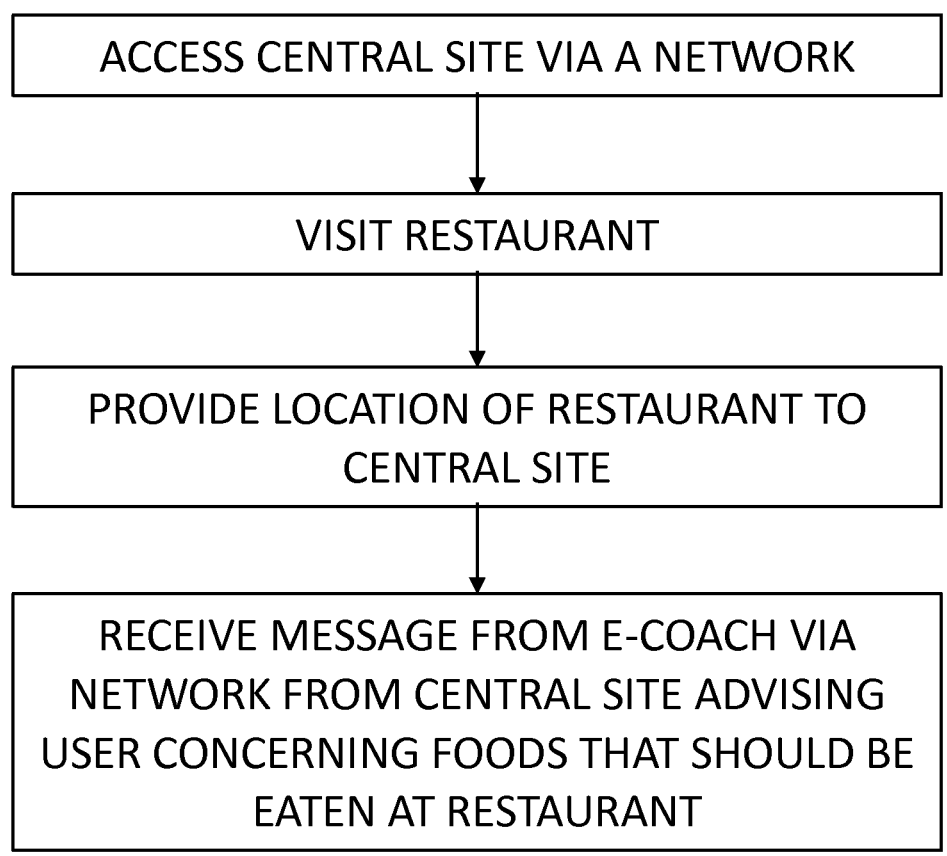
FIG. 2 is a flowchart illustrating an embodiment of the inventive method useful in maintaining a diet or nutrition plan.

In FIG. 2, an embodiment of the inventive method useful in following a diet or nutritional plan is illustrated. A user who desires to follow a particular diet or nutritional plan accesses the central site via a PDA or other portable device. In more specific embodiments, the user provides the central site with details of the particular diet or nutritional plan he desires to follow, either prior to or subsequent accessing the central site via his PDA or other portable device. Next, the user visits a restaurant, bar or other physical location at which food and/or drink is served. The user provides location information to the central site, for example, the GPS coordinates of the restaurant, a code identifying the restaurant, or the like. The user then receives advice pertaining to his diet or nutritional plan from the central site.

In particular embodiments, the user specifies that the central site is to provide periodic reminders to the user to follow his diet or nutritional plan, the reminders to be delivered while the user is present at the restaurant These reminders can be pre-recorded text or audio messages, or reminders from one or more e-coaches via the central site. In other particular embodiments, the user requests to receive advice from an e-coach via the central site concerning specific menu items, beverages, etc. For example, the user can request advice from an e-coach as to whether a particular item can be consumed within the limits of the user's diet or nutritional plan, and if so, the quantity that can be consumed.

In additional embodiments, when the user patronizes a restaurant which is included in a database stored in the central site, the user is provided with information pertaining to item(s) the user desires to order. Such information can include, for example, calories, sodium content, carbohydrate content, etc., and can be provided to the user via a PDA or other device. The user can also be provided with the option of receiving real-time advice from a dietitian or other nutritional professional (in particular embodiments, for a fee). Such advice can include encouragement to avoid or reduce consumption of specific foods and/or beverages, including in particular the item(s) ordered or intended to be ordered by the user.

To encourage participation by restaurants and other food and/or beverage serving establishments, and to avoid occurrences of a user canceling an order after being advised to do so according to the inventive method and then leaving the establishment without ordering, particular embodiments provide for an automatic minimum charge to be assessed to the user upon entry into the establishment.

In specific embodiments, the restaurant or other establishment serving foods and/or beverages is listed in the database on the central site, as mentioned above. In other specific embodiments, the establishment is not included in the database, but has a GPS location. In such embodiments, a user can receive a message indicating that the establishment is "off-network", or receive a message from the central site or a dietitian or other nutrition professional offering to assist the user in adhering to his dietary plan. Such advice can include, for example, an offer to assist the user in ordering one or more food and/or beverage items.

Other embodiments of the inventive method are useful in following an exercise plan. In these embodiments, the user accesses the central site as above. When the user visits a health club, gymnasium or other physical location where exercises are to be performed, the user provides the central site with location information pertaining to the health club or other location. The user then receives advice via the central site concerning the performance of his exercise plan.

E-coaching advice can be provided to the user without charge, or in particular embodiments, upon payment of a per-use or periodic fee.

Figure 3:
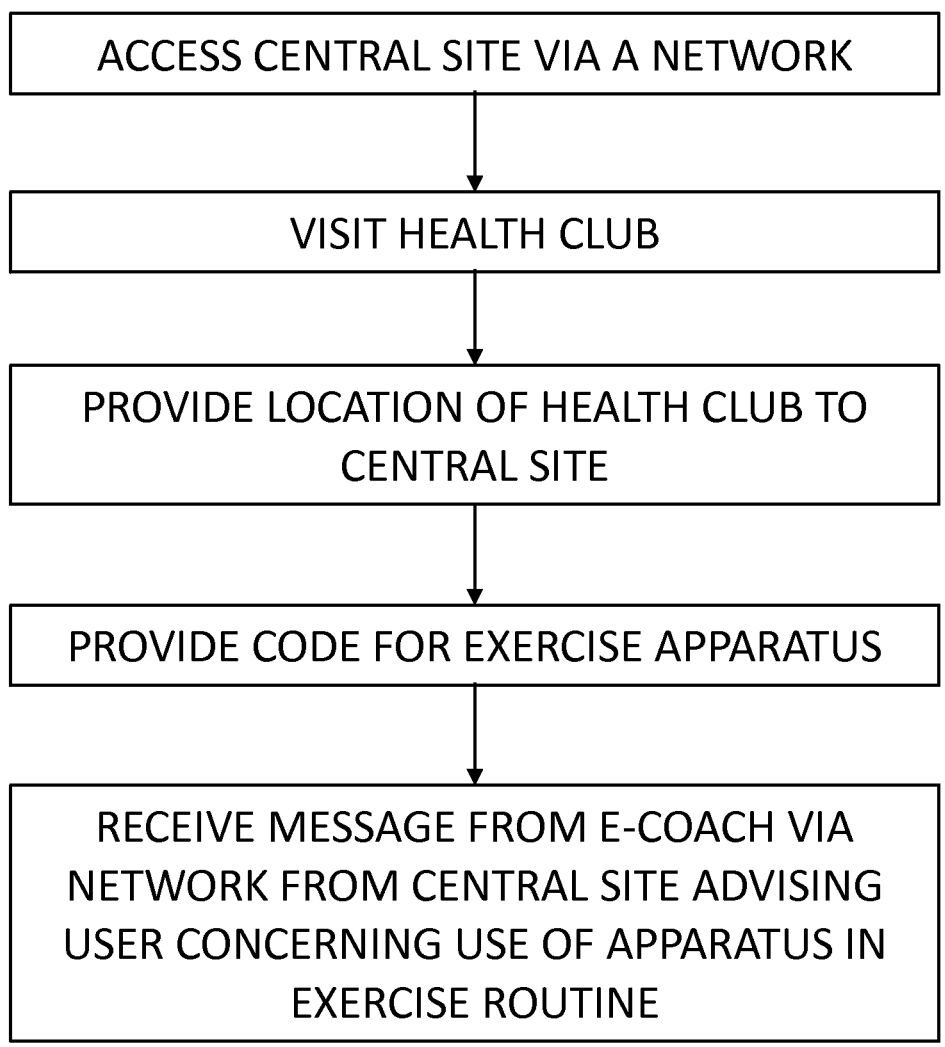
FIG. 3 is a flowchart illustrating an embodiment of the inventive method useful in performing an exercise plan.

In FIG. 3, an embodiment of the inventive method useful in following an exercise plan is illustrated. The user accesses the central site, then visits a health club. The user next provides the central site with location or other identifying information associated with the health club and with a specific exercise apparatus. The central site then provides the user with advice pertaining to use of the apparatus. For example, the central site can provide the user with the number of repetitions to be performed per set on the selected apparatus, the weight to be used during each set, the time interval between each set, etc. This advice can be provided by one or more e-coaches, by means of computer-generated messages, or the like, as described previously. Alternatively, a user's PDA can ping each piece of equipment and receive advice pertaining to the piece of equipment, or GPS coordinates can be used in order to facilitate provision of advice to the site so identified.

According to a variant of the foregoing embodiment, a user first visits a health club, and then accesses the central site. The health club visited by the user is identified by its GPS coordinates, as are all pieces of equipment on site at the health club.

In another alternative embodiment, a piece of equipment is identified, e.g., by its GPS coordinates, and associated with the user. Once the piece of equipment has been associated with the user, a record including information on the user's previous use of the equipment can be accessed, via, e.g., the user's PDA, an integral network accessing device, or the like. For example, the record can inform the user that on his last use of the piece of equipment, he performed twenty repetitions at 50 lbs. During or after completion of the user's performance on the piece of equipment, the record can be updated accordingly. The updating can be carried out by the user, or can be performed automatically by the piece of equipment itself.

Real-time coaching advice from an e-coach observing the user in real time can also be provided to the user in alternative embodiments of the inventive method. For example, a piece of equipment can be provided with a camera, which enables a professional trainer to observe the user's performance on the piece of equipment over a network, such as the Internet. Such real-time e-coaching can be provided as a service by the health club for which an additional fee is charged per use (for example, at a rate of $1.00/min). Alternatively, the service can be billed to the user periodically (e.g., added to monthly dues) with unlimited or limited access by the user during the billing period. Known security methods can be applied to ensure proper use and billing. For example, per-use charges can be billed to the user's credit card using known security procedures.

In particular embodiments, the central site retains a record of the users performance on one or more specified exercise devices. This record can be made available to the user so that the user can monitor his progress.

In more particular embodiments, the user specifies a plurality of different exercise apparatus, and is provided with advice pertaining to the use of each selected apparatus. In still other particular embodiments, the user receives advice concerning the selection of one or more exercise apparatus, and in embodiments selecting a plurality of apparatus, additional advice concerning the sequence of use of each selected apparatus.

Related alternative embodiments are beneficially implemented in the context of any activity which subjects the user to "temptation", for example, casino gambling, patronization of massage parlors, etc. Thus, a user can, in particular embodiments, enter a casino or massage parlor and receive a real-time message, either from an advisor such as a psychiatrist, religious advisor or other professional, or alternatively a recorded message from such professionals or others (e.g., the user's spouse or parent) urging the user to desist from the activity.

What is claimed is:

1. A method of obtaining advice pertaining to a fitness-related activity performed by a user using one or more pieces of equipment, the method comprising:

accessing a central site on a communication network using a portable network access device;

obtaining, with the portable network access device, GPS location information corresponding to a physical location associated with a fitness-related activity while the user carries the portable network access device;

providing the GPS location information to the central site over the network with the portable network access device, the location information being associated with a record of previous use, by the user, of equipment located at the physical location; and while the user is at the physical location, receiving advice information on the portable network access device, over the network from the central site, wherein the advice information pertains to use of the equipment located at the physical location and wherein the advice information is based on the record of previous use by the user of the equipment located at the physical location.

2. A method of obtaining advice pertaining to performance of an exercise by a user employing at least one exercise apparatus, the method comprising:

accessing a central site on a communication network using a portable network access device;

obtaining, with the portable network access device, GPS location information corresponding to a physical location at which at least one exercise apparatus is present;

providing the GPS location information to the central site over the network with the portable network access device;

receiving, at the portable network access device, from a particular exercise apparatus present at the physical location, information regarding the particular exercise apparatus;

providing to the central site the information regarding the particular exercise apparatus; and receiving advice information on the portable network access device, over the network from the central site, wherein the advice information pertains to use by the user of the particular exercise apparatus.

3. A method of obtaining advice pertaining to an activity performed by a user on at least one piece of fitness equipment, the method comprising:

accessing a central site on a communication network using a portable network access device carried by the user while visiting a physical location;

obtaining, with the portable network access device, GPS location information corresponding to the physical location, while the user visits the physical location;

while the user visits the physical location, providing the GPS location information to the central site over the network with the portable network access device, the location information being associated with a record of previous use, by the user, of fitness equipment located at the physical location; and while the user visits the physical location, receiving advice information on the portable network access device, over the network from the central site, wherein the advice information pertains to use of the fitness equipment located at the physical location, wherein the advice information is based on the record of previous use, by the user, of the fitness equipment located at the physical location, and wherein the advice information comprises advice pertaining to one or more of the following:

a number of repetitions of exercise activities to perform using the fitness equipment located at the physical location, an amount of weight for the user to use when performing exercise activities using the fitness equipment located at the physical location, or an amount of time relating to exercise activities using the fitness equipment located at the physical location;

accepting a signal to update the record of previous use, by the user, of the fitness equipment located at the physical location after completion of use of the fitness equipment located at the physical location; and transmitting to the central site via the network a request to update the record based on the user's completed use of the fitness equipment located at the physical location.

4. The method of claim 1 wherein the advice information comprises a live message from a personal advisor.

5. The method of claim 1 wherein the central site arranges for at least one personal advisor to directly contact the user.

6. The method of claim 2 wherein the at least one exercise apparatus comprises a camera which enables a personal advisor to observe the user's performance on the at least one exercise apparatus.

7. The method of claim 1 wherein the advice information is provided in exchange for a per-use or periodic fee.

8. The method of claim 2 wherein the advice information is provided in exchange for a per-use or periodic fee.

9. The method of claim 1 wherein receiving advice information comprises receiving information that corresponds to the user's previous use of a plurality of pieces of fitness equipment located at the physical location.

10. The method of claim 9 wherein providing GPS location information to the central site comprises providing GPS location information associated with the location of a plurality of pieces of fitness equipment located at the physical location.

11. A method of providing advice over a communication network having a central site, the advice pertaining to a fitness-related activity performed by a network user using one or more pieces of fitness equipment, the network user having a communication device communicatively connected to the communication network, the method comprising:

receiving GPS location information at the central site from a network user while the network user is visiting a physical location associated with a fitness-related activity;

associating the network user with a piece of fitness equipment located at the physical location;

associating the GPS location information with a record retained by the central site, the record including previously-stored information about the network user's previous use of the piece of fitness equipment located at the physical location;

accessing the record; and transmitting advice information over the network from the central site to the network user's communication device, wherein the advice information pertains to use of the fitness equipment located at the physical location and wherein the advice information comprises information based on the record.

12. The method of claim 11 wherein transmitting advice information comprises transmitting information that corresponds to the network user's previous use of a plurality of pieces of fitness equipment located at the physical location.

13. The method of claim 12 wherein receiving location information at the central site comprises receiving location information associated with the location of the plurality of pieces of fitness equipment located at the physical location.

14. A method of providing advice over a communication network, the advice pertaining to a fitness-related activity performed by a network user using one or more pieces of fitness equipment, the network user having a communication device communicatively connected to the communication network, the method comprising:

receiving GPS location information at a central site from the communication device while the network user is visiting a physical location associated with a fitness-related activity;

receiving fitness equipment information at the central site from the communication device while the network user is visiting the physical location associated with the fitness-related activity;

identifying fitness equipment at the physical location from one or more of the GPS location information and the fitness equipment information;

accessing a record pertaining to prior use of the fitness equipment by the user; and transmitting advice information over the network from the central site to the network user's communication device, wherein the advice information pertains to use of the fitness equipment by the user and wherein the advice information is based on the record.

15. The method of claim 1, wherein the advice information comprises information regarding previous use by the user of the equipment located at the physical location.

16. The method of claim 2, wherein the advice information comprises information regarding previous use by the user of the at least one exercise apparatus located at the physical location.

17. The method of claim 11, wherein the advice information comprises information regarding the network user's previous use of the piece of equipment located at the physical location.

18. The method of claim 14, wherein the advice information comprises information regarding the network user's previous use of the piece of equipment located at the physical location.

19. The method of claim 1, wherein the advice information comprises advice regarding a number of repetitions of exercise activities to perform using the equipment located at the physical location.

20. The method of claim 1, wherein the advice information comprises advice regarding an amount of weight for the user to use when performing exercise activities using the equipment located at the physical location.

21. The method of claim 1, wherein the advice information comprises advice regarding an amount of time relating to exercise activities using the equipment located at the physical location.

22. The method of claim 9, wherein the advice information comprises advice pertaining to a sequence of use of the plurality of pieces of fitness equipment located at the physical location.

23. The method of claim 1, further comprising:
accepting a signal to update the record of previous use after completion of use of the equipment located at the physical location; and
transmitting to the central site via the network a request to update the record based on the user's completed use of the equipment located at the physical location.

24. The method of claim 1, wherein providing the GPS location information to the central site over the network with the portable network access device occurs while the user is at the physical location associated with the fitness-related activity.

25. The method of claim 2, wherein the advice information comprises advice regarding a number of repetitions of exercise activities to perform using the at least one exercise apparatus located at the physical location.

26. The method of claim 2, wherein the advice information comprises advice regarding an amount of weight for the user to use when performing exercise activities using the at least one exercise apparatus located at the physical location.

27. The method of claim 2, wherein the advice information comprises advice regarding an amount of time relating to exercise activities using the at least one exercise apparatus located at the physical location.

28. The method of claim 2, wherein providing the GPS location information to the central site over the network with the portable network access device occurs while the user is at the physical location at which the at least one exercise apparatus is present.

29. The method of claim 11, wherein the advice information comprises advice regarding a number of repetitions of exercise activities to perform using the fitness equipment located at the physical location.

30. The method of claim 11, wherein the advice information comprises advice regarding an amount of weight for the user to use when performing exercise activities using the fitness equipment located at the physical location.

31. The method of claim 11, wherein the advice information comprises advice regarding an amount of time relating to exercise activities using the fitness equipment located at the physical location.

32. The method of claim 11, further comprising:
updating the record, after completion of use of the equipment located at the physical location, based on the user's completed use of the equipment located at the physical location.

33. The method of claim 14, wherein the advice information comprises advice regarding a number of repetitions of exercise activities to perform using the fitness equipment located at the physical location.

34. The method of claim 14, wherein the advice information comprises advice regarding an amount of weight for the user to use when performing exercise activities using the fitness equipment located at the physical location.

35. The method of claim 14, wherein the advice information comprises advice regarding an amount of time relating to exercise activities using the fitness equipment located at the physical location.

36. The method of claim 14, further comprising:
updating the record, after completion of use of the equipment located at the physical location, based on the user's completed use of the equipment located at the physical location.

* * * * *